(12) United States Patent
Liu et al.

(10) Patent No.: US 11,655,141 B2
(45) Date of Patent: May 23, 2023

(54) FABRICATION TECHNIQUES AND STRUCTURES FOR GETTERING MATERIALS IN ULTRASONIC TRANSDUCER CAVITIES

(71) Applicant: BFLY OPERATIONS, INC., Burlington, MA (US)

(72) Inventors: Jianwei Liu, Fremont, CA (US); Keith G. Fife, Palo Alto, CA (US); Joseph Lutsky, Los Altos, CA (US); Lingyun Miao, Fremont, CA (US)

(73) Assignee: BFLY OPERATIONS, INC., Burlington, MA (US)

( * ) Notice: Subject to any disclaimer, the term of this patent is extended or adjusted under 35 U.S.C. 154(b) by 657 days.

(21) Appl. No.: 16/585,283

(22) Filed: Sep. 27, 2019

(65) Prior Publication Data

US 2020/0102214 A1    Apr. 2, 2020

Related U.S. Application Data

(60) Provisional application No. 62/738,502, filed on Sep. 28, 2018.

(51) Int. Cl.
*B81B 7/00* (2006.01)
*B81C 1/00* (2006.01)
*H04R 31/00* (2006.01)
*A61B 8/00* (2006.01)
(Continued)

(52) U.S. Cl.
CPC .......... *B81B 7/0038* (2013.01); *A61B 8/4483* (2013.01); *B81C 1/00158* (2013.01); *G10K 13/00* (2013.01); *H04R 31/003* (2013.01); *B81B 2201/0271* (2013.01); *G10K 11/28* (2013.01)

(58) Field of Classification Search
CPC .......... B81B 7/0038; B81B 2201/0271; A61B 8/4483; B81C 1/00158; B81C 1/00285; G10K 13/00; G10K 11/28; H04R 31/003; H04R 19/005; B06B 1/0292
See application file for complete search history.

(56) References Cited

U.S. PATENT DOCUMENTS

| | | |
|---|---|---|
| 6,430,109 B1 | 8/2002 | Khuri-Yakub et al. |
| 6,694,817 B2 | 2/2004 | Degertekin et al. |
| 6,779,387 B2 | 8/2004 | Degertekin |

(Continued)

FOREIGN PATENT DOCUMENTS

| | | | |
|---|---|---|---|
| JP | 2005235452 A * | 9/2005 | .............. H01J 31/12 |
| WO | WO 2013/049794 A1 | 4/2013 | |
| WO | WO 2016/011000 | 1/2016 | |

OTHER PUBLICATIONS

Daft et al., Microfabricated ultrasonic transducers monolithically integrated with high voltage electronics. Proc Ultrason Symp. 2004;493-6.

(Continued)

*Primary Examiner* — Oyesola C Ojo
(74) *Attorney, Agent, or Firm* — Osha Bergman Watanabe & Burton LLP

(57) ABSTRACT

A method of forming an ultrasound transducer device includes bonding a membrane to a substrate so as to form a sealed cavity between the membrane and the substrate. An exposed surface located within the sealed cavity includes a getter material that is electrically isolated from a bottom electrode of the cavity.

16 Claims, 10 Drawing Sheets

(51) Int. Cl.
*G10K 13/00* (2006.01)
*G10K 11/28* (2006.01)

(56) References Cited

U.S. PATENT DOCUMENTS

| | | | |
|---|---|---|---|
| 6,958,255 | B2 | 10/2005 | Khuri-Yakub et al. |
| 7,615,834 | B2 | 11/2009 | Khuri-Yakub et al. |
| 7,846,102 | B2 | 12/2010 | Kupnik et al. |
| 8,241,931 | B1 | 8/2012 | Antoine et al. |
| 8,402,831 | B2 | 3/2013 | Kupnik et al. |
| 9,067,779 | B1 | 6/2015 | Rothberg et al. |
| 9,143,868 | B2 * | 9/2015 | Pinkerton ............... H04R 19/02 |
| 9,242,275 | B2 | 1/2016 | Rothberg et al. |
| 9,319,800 | B2 | 4/2016 | Hong et al. |
| 9,499,392 | B2 | 11/2016 | Rothberg et al. |
| 9,505,030 | B2 | 11/2016 | Rothberg et al. |
| 9,533,873 | B2 | 1/2017 | Rothberg et al. |
| 9,938,134 | B2 | 4/2018 | Lin et al. |
| 2004/0141421 | A1 | 7/2004 | Cheng et al. |
| 2007/0215964 | A1 | 9/2007 | Khuri-Yakub et al. |
| 2009/0085205 | A1 * | 4/2009 | Sugizaki ............... B81B 7/007 257/E21.59 |
| 2009/0140609 | A1 | 6/2009 | Huang |
| 2010/0225200 | A1 | 9/2010 | Kupnik et al. |
| 2011/0018398 | A1 * | 1/2011 | Fukuda ............... H03H 9/02149 29/25.35 |
| 2011/0050045 | A1 | 3/2011 | Aratake et al. |
| 2011/0055447 | A1 | 3/2011 | Costa |
| 2011/0115333 | A1 | 5/2011 | Ezaki |
| 2013/0135056 | A1 * | 5/2013 | Allegata ............... H03B 5/32 331/116 R |
| 2014/0264660 | A1 | 9/2014 | Rothberg et al. |
| 2016/0009544 | A1 | 1/2016 | Rothberg et al. |
| 2016/0043660 | A1 | 2/2016 | Wang et al. |
| 2017/0232474 | A1 | 8/2017 | Oralkan et al. |
| 2018/0243792 | A1 | 8/2018 | Rothberg et al. |
| 2018/0369862 | A1 | 12/2018 | Alie et al. |
| 2018/0376253 | A1 | 12/2018 | Lutsky et al. |
| 2019/0047850 | A1 | 2/2019 | Rothberg et al. |
| 2019/0142387 | A1 | 5/2019 | Chen et al. |
| 2019/0160490 | A1 | 8/2019 | Alie et al. |
| 2019/0231312 | A1 | 8/2019 | Fife et al. |
| 2019/0261954 | A1 | 8/2019 | Chen et al. |
| 2019/0261955 | A1 | 8/2019 | Chen et al. |
| 2019/0275561 | A1 | 9/2019 | Fife et al. |
| 2019/0336099 | A1 | 11/2019 | Fife et al. |
| 2019/0336103 | A1 | 11/2019 | Fife et al. |
| 2019/0336104 | A1 | 11/2019 | Fife et al. |
| 2020/0013691 | A1 | 1/2020 | Liu et al. |
| 2020/0324318 | A1 | 10/2020 | Liu et al. |
| 2020/0324319 | A1 | 10/2020 | Miao et al. |

OTHER PUBLICATIONS

Gurun et al., Front-end CMOS electronics for monolithic integration with CMUT arrays: circuit design and initial experimental results. Proc Ultrason Symp. 2008;390-3.
Kupnik et al., CMUT Fabrication Based On A Thick Buried Oxide Layer. Proc IEEE Ultrason Symp. Oct. 2010;2010:547-550. doi:10.1109/ULTSYM.2010.5935935. Epub Jun. 8, 2012. 10 pages.
Kupnik et al., Wafer-Bonded CMUT Meets CMOS. 2010 CMOS Emerging Technology Workshop. May 21, 2010;1-22.
International Search Report and Written Opinion dated Dec. 16, 2019 in connection with International Application No. PCT/US2019/053352.
International Preliminary Report on Patentability dated Apr. 8, 2021 in connection with International Application No. PCT/US2019/053352.
International Search Report and Written Opinion dated Jul. 13, 2020 in connection with International Application No. PCT/US2020/027437.
International Search Report and Written Opinion dated Jul. 13, 2020 in connection with International Application No. PCT/US2020/027457.
U.S. Appl. No. 16/844,857, filed Apr. 9, 2020, Miao.
U.S. Appl. No. 16/844,837, filed Apr. 9, 2020, Liu et al.
PCT/US2019/053352, Apr. 8, 2021, International Preliminary Report on Patentability.
PCT/US2020/027437, Jul. 13, 2020, International Search Report and Written Opinion.
PCT/US2020/027457, Jul. 13, 2020, International Search Report and Written Opinion.
Extended European Search Report for European Application No. 19868109.0 dated Sep. 30, 2022.
International Preliminary Report on Patentability dated Oct. 21, 2021 in connection with International Application No. PCT/US2020/027457.
EP 19868109.0, Sep. 30, 2022, Extended European Search Report.
PCT/US2020/027457, Oct. 21, 2021, International Preliminary Report on Patentability.

* cited by examiner

FABRICATION TECHNIQUES AND STRUCTURES FOR GETTERING MATERIALS IN ULTRASONIC TRANSDUCER CAVITIES

CROSS-REFERENCE TO RELATED APPLICATIONS

The present application claims the benefit under 35 U.S.C. § 119(e) of U.S. Patent Application Ser. No. 62/738,502, filed Sep. 28, 2018 under No. B1348.70103US00, and entitled "FABRICATION TECHNIQUES AND STRUCTURES FOR GETTERING MATERIALS IN ULTRASONIC TRANSDUCER CAVITIES," which is hereby incorporated herein by reference in its entirety.

FIELD

The present disclosure relates generally to micromachined ultrasound transducers and, more specifically, to fabrication techniques and associated structures for gettering materials present in ultrasound transducer cavities during manufacture.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasound transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, an output electrical signal can be generated.

SUMMARY

In one aspect, a method of forming an ultrasound transducer device includes bonding a membrane to a substrate so as to form a sealed cavity therebetween, wherein an exposed surface located within the sealed cavity comprises a getter material, the getter material being electrically isolated from a bottom electrode of the cavity.

In another aspect, an ultrasound transducer device includes a membrane bonded to a substrate with a sealed cavity therebetween. An exposed surface located within the sealed cavity includes a getter material, the getter material being electrically isolated from a bottom electrode of the cavity.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 10-19 illustrate a process flow sequence for forming the ultrasound transducer embodiments of FIGS. 1-9, in which:

FIG. 10 illustrates the formation of an electrode layer over a CMOS substrate.

FIG. 11-1 illustrates patterning of the electrode layer of FIG. 10 according to the embodiment of FIG. 1.

FIG. 11-2 illustrates patterning of the electrode layer of FIG. 10 according to the embodiment of FIG. 4.

FIG. 11-3 illustrates patterning of the electrode layer of FIG. 10 according to the embodiment of FIG. 7.

FIG. 12-1 illustrates forming an insulation layer over the structure of FIG. 11-1.

FIG. 12-2 illustrates forming an insulation layer over the structure of FIG. 11-2.

FIG. 12-3 illustrates forming an insulation layer over the structure of FIG. 11-3.

FIG. 13-1 illustrates planarizing the insulation layer of the structure of FIG. 12-1.

FIG. 13-2 illustrates planarizing the insulation layer of the structure of FIG. 12-2.

FIG. 13-3 illustrates planarizing the insulation layer of the structure of FIG. 12-3.

FIG. 14 illustrates forming an insulation stack over the structure of FIG. 13-1.

FIG. 15 illustrates forming a cavity in the insulation stack.

FIG. 16 illustrates removing a portion of the lower insulation layers of the insulation stack to expose adjacent electrode material that serves as a getter material.

FIG. 17 illustrates a silicon-on-insulator (SOI) wafer to be bonded to the structure of FIG. 16.

FIG. 18 illustrates the SOI wafer bonded to the structure of FIG. 16.

FIG. 19 illustrates removing a portion of the SOI wafer to define a membrane of a micromachined ultrasound transducer.

DETAILED DESCRIPTION

One type of transducer suitable for use in ultrasound imaging devices is a micromachined ultrasound transducer (MUT), which can be fabricated from, for example, silicon and configured to transmit and receive ultrasound energy. MUTs may include capacitive micromachined ultrasound transducers (CMUTs) and piezoelectric micromachined ultrasound transducers (PMUTs), which can offer several advantages over more conventional ultrasound transducer designs such as, for example, lower manufacturing costs and fabrication times and/or increased frequency bandwidth. With respect to the CMUT device, the basic structure is a parallel plate capacitor with a rigid bottom electrode and a top electrode residing on or within a flexible membrane. Thus, a cavity is defined between the bottom and top electrodes. In some designs (such as those produced by the assignee of the present application for example), the CMUT transducer may be directly integrated on an integrated circuit that controls the operation of the transducer. One way of manufacturing a CMUT ultrasound device is to bond a membrane substrate to an integrated circuit substrate, such as a complementary metal oxide semiconductor (CMOS) substrate. This may be performed at temperatures sufficiently low to prevent damage to the devices of the integrated circuit.

However, during bonding of the membrane substrate to the CMOS substrate, there may be a difference in cavity pressures across the die and wafer due to the water vapor and other gaseous byproducts and the propagation of the bond. This in turn may result in undesired variability of certain CMUT-based operating parameters such as for example, collapse voltage, as well as transmit/receive pressure sensitivity. Accordingly, it is desirable to be able to control cavity pressure within such a transducer device during the manufacturing process, as well as over the lifetime of the device.

Figure 1:
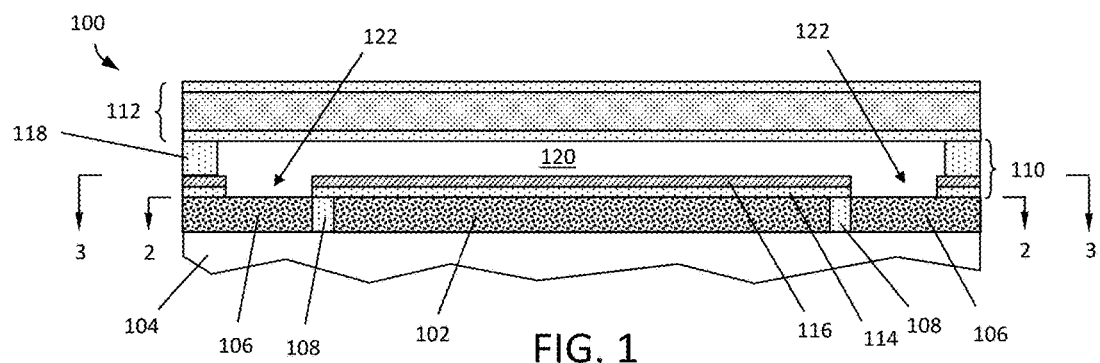
FIG. 1 is a cross-sectional view of a micromachined ultrasound transducer having a cavity getter material, in accordance with an embodiment.

Referring now to FIG. 1, there is shown a cross-sectional view of a micromachined ultrasound transducer 100 having a cavity getter material, in accordance with an embodiment. As is shown, the ultrasound transducer 100 includes a lower electrode 102 formed over a substrate 104 (e.g., a CMOS substrate, such as silicon). The CMOS substrate 104 may include, but is not necessarily limited to, CMOS circuits, wiring layers, redistribution layers, and insulation/passivation layers. In an exemplary embodiment, suitable materials for the lower electrode 102 include one or more of titanium (Ti), zirconium (Zr), vanadium (V), cobalt (Co), nickel (Ni), as well as alloys thereof.

Figure 2:
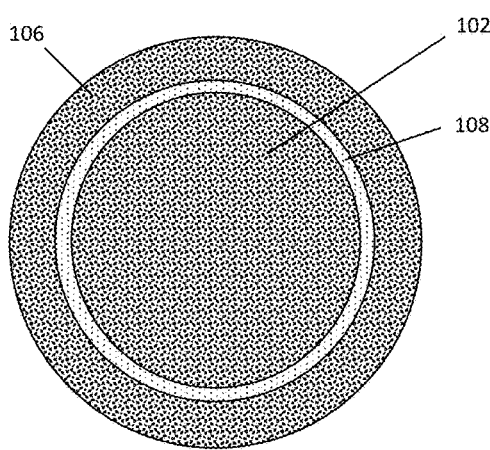
FIG. 2 is a top view of the ultrasound transducer of FIG. 1, taken along the arrows 2-2.

As further shown in FIG. 1, the lower electrode 102 is electrically isolated from adjacent metal regions 106 that are also formed on the substrate 104. Exposed portions of the adjacent metal regions 106 may thus serve as a getter material during cavity formation. The adjacent metal regions 106 may be formed from a same metal material as the lower electrode 102, and are electrically isolated from the lower electrode 102 by an insulator material 108 (e.g., silicon oxide). By way of further illustration, FIG. 2 is a top down view of the lower electrode, adjacent metal regions 106 and insulator material 108, taken along the arrows 2-2 in FIG. 1. It should be appreciated that although the exemplary geometric structure of this portion of the ultrasound transducer 100 is generally circular in shape, other configurations are also contemplated such as for example, rectangular, hexagonal, octagonal, and other multi-sides shapes, etc.

Referring again to FIG. 1, an insulator layer (e.g., one or more individual insulator layers, such as an insulator stack 110) is formed over the lower electrode 102 and portions of adjacent metal regions 106. Portions of the stack 110 provide support for a moveable membrane 112 (e.g., an SOI wafer having a doped silicon device layer with an oxidized surface) bonded to the stack 110. In the illustrated embodiment, the insulator stack 110 includes a first oxide layer 114 (e.g., chemical vapor deposition (CVD) silicon oxide), a second oxide layer 116 (e.g., atomic layer deposition (ALD) aluminum oxide) and a third oxide layer 118 (e.g., sputter deposited silicon oxide). By suitable lithographic patterning and etching of the third oxide layer 118, a cavity 120 may be defined for the ultrasound transducer 100. Further, in embodiments where the second oxide layer 116 is chosen from a material having an etch selectivity with respect to the third oxide layer 118, the second oxide layer 116 may serve as an etch stop for removing portions of the third oxide layer 118 in order to define the cavity 120.

Figure 3:
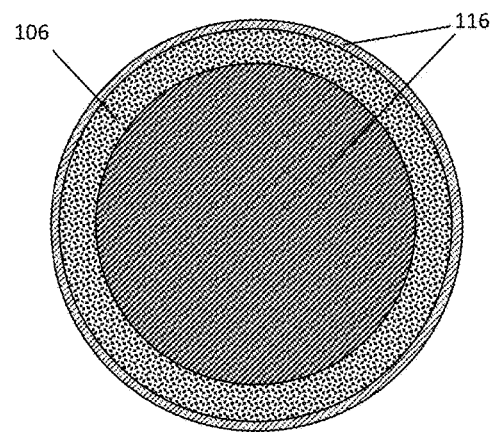
FIG. 3 is a top view of the ultrasound transducer of FIG. 1, taken along the arrows 3-3.

In addition to the etch of the third oxide layer that defines the cavity 120, another etch is used to define openings 122 through the second oxide layer 116 and first oxide layer 114, thereby exposing a top surface of a portion of metal regions 106. A top down view of the cavity 120, illustrating remaining portions of the second oxide layer 116 and the exposed portions of metal regions is illustrated in FIG. 3, taken along the arrows 3-3 in FIG. 1. The exposed portions of metal regions 106 may advantageously serve as a getter material of one or more gases present during a bonding operation of the membrane 112 to seal the cavity 120. Additional exemplary processing operations used in forming the ultrasound transducer 100 are discussed hereinafter.

Figure 4:
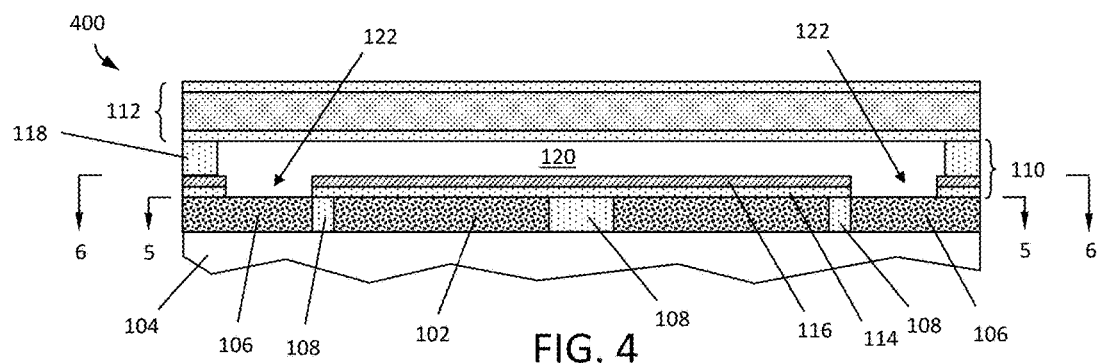
FIG. 4 is a cross-sectional view of a micromachined ultrasound transducer having a cavity getter material, in accordance with another embodiment.
Figure 5:
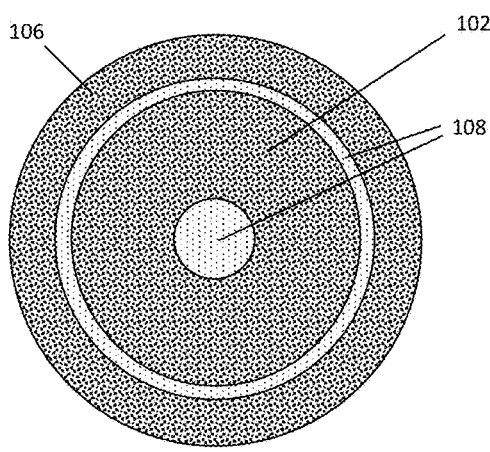
FIG. 5 is a top view of the ultrasound transducer of FIG. 4, taken along the arrows 5-5.
Figure 6:
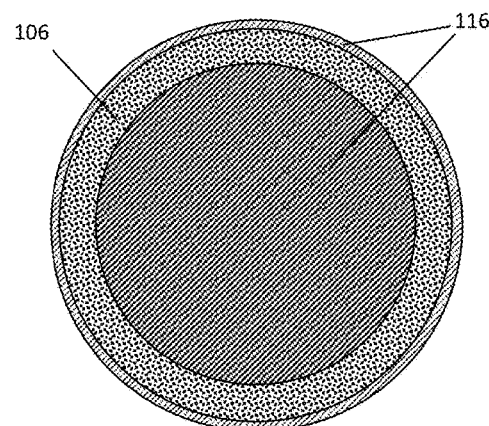
FIG. 6 is a top view of the ultrasound transducer of FIG. 4, taken along the arrows 6-6.

It will be appreciated that the gettering technique and associated removal of a portion of oxide layers 116 and 114 to expose a portion of metal regions 106 can be implemented in conjunction with any of a number of transducer electrode structures. For example, FIGS. 4-6 illustrate a cross-sectional and top down views of a micromachined ultrasound transducer 400 having a cavity getter material, in accordance with another embodiment. For ease of description, like elements are designated by like reference numerals in the various embodiments. As particularly illustrated in FIG. 4 and in FIG. 5 (taken along the lines 5-5 in FIG. 4) the lower electrode 102 is formed so as to have a "donut" pattern; that is, a region corresponding to the innermost radius of the electrode structure of the earlier described embodiment is instead formed from an insulating material (e.g., oxide 108) rather than the conductive electrode material. It will be noted that since oxide layers 116 and 114 are only removed from the outer region of the cavity geometry, the top down view of FIG. 6 is substantially similar to that of the embodiment of FIG. 3.

The electrode geometry of FIG. 4 may be employed in various operating modes, including in conjunction with a collapse mode of operation of the ultrasound transducer 400, where at least a part of the membrane 112 comes into physical contact with a bottom surface of the cavity 120 (for example, second oxide layer 116). In this case, substituting a central portion of the lower electrode material with an insulator material can help to reduce parasitic capacitance of the ultrasound transducer 400 without significantly compromising performance, as the central portion of the electrode in physical contact with the bottom of the ultrasound transducer cavity has a minimum contribution to the production of ultrasonic signals. Still a further benefit to such an electrode structure may be the reduction of charging on the membrane 112 otherwise caused by repeated collapsing. Additional information regarding a donut shaped lower electrode may be found in U.S. Patent Application Ser. No. 62/666,643, filed May 3, 2018 and assigned to the assignee of the present application, and in co-pending U.S. patent application Ser. No. 16/401,630, filed May 2, 2019 and assigned to the assignee of the present application, the contents of both of which are incorporated by reference herein in their entireties.

Figure 7:
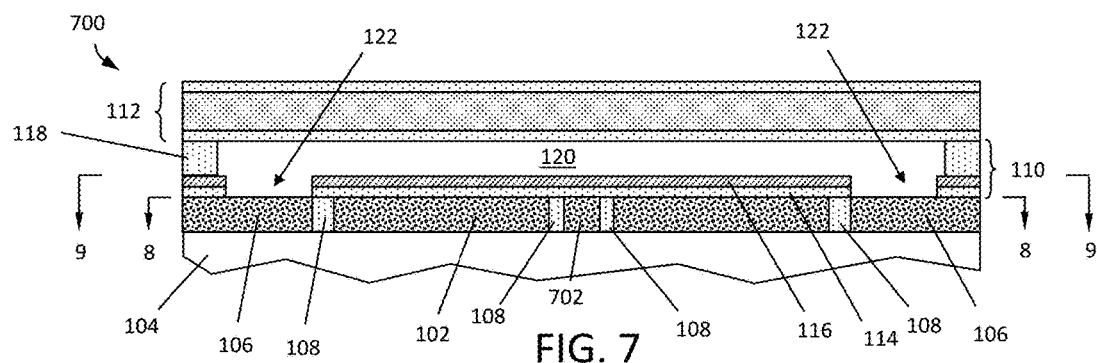
FIG. 7 is a cross-sectional view of a micromachined ultrasound transducer having a cavity getter material, in accordance with another embodiment.
Figure 8:
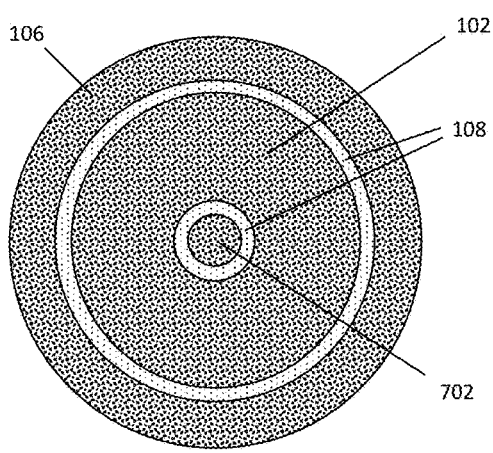
FIG. 8 is a top view of the ultrasound transducer of FIG. 7, taken along the arrows 8-8.
Figure 9:
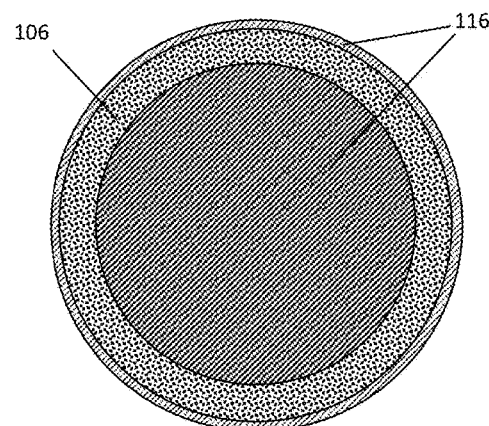
FIG. 9 is a top view of the ultrasound transducer of FIG. 7, taken along the arrows 9-9.

Referring now to FIGS. 7-9, there is illustrated a cross-sectional and top down views of a micromachined ultrasound transducer 700 having a cavity getter material, in accordance with still another embodiment. Again, for ease of description, like elements are designated by like reference numerals in the various embodiments. As particularly illustrated in FIG. 7 and in FIG. 8 (taken along the lines 8-8 in FIG. 7) the lower electrode 102 is still formed so as to have a "donut" pattern. However, in contrast to the embodiment of FIGS. 4-6, an additional electrode 702 is formed at the central portion of the cavity region. The electrode 702 is patterned to be electrically isolated from lower electrode 102, such as by being insulated therefrom by oxide 108 for example. As is the case with the other embodiments, the top down view of FIG. 9 is substantially similar to that of the embodiments of FIG. 3 and FIG. 6.

An electrode geometry of the type shown in FIG. 7, in addition to the benefits described with respect to the previous embodiment, can also contribute to a bypass capacitance between the membrane 112 and ground, which in turn may contribute to noise reduction on the voltage of the membrane 112. Another benefit of electrode 702 may be to help provide for a lower collapse voltage for the ultrasound transducer 700 by way of the electrode 702 attracting the membrane 112 toward the bottom of the cavity 120. Additional information regarding this electrode design may also be found in the aforementioned co-pending U.S. Patent Application Ser. No. 62/666,643 and Ser. No. 16/401,630.

Figure 10:
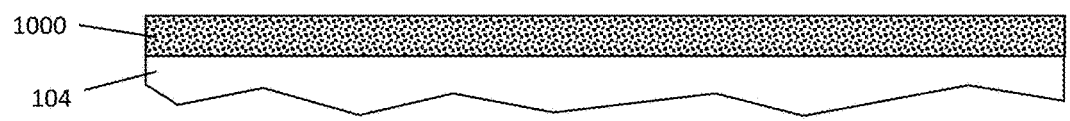

Referring generally now to FIGS. 10-19, there is shown an exemplary process flow sequence for forming the ultrasound transducer embodiments described above. In FIG. 10, an electrode layer 1000 is formed over CMOS substrate 104, such as a silicon substrate for example. Again, the CMOS substrate 104 may include, but is not necessarily limited to, CMOS circuits, wiring layers, redistribution layers, and insulation/passivation layers. As also mentioned previously, suitable materials for the electrode layer 1000 include one more of titanium (Ti), zirconium (Zr), vanadium (V), cobalt (Co), nickel (Ni), as well as alloys thereof.

Figures 1, 11:
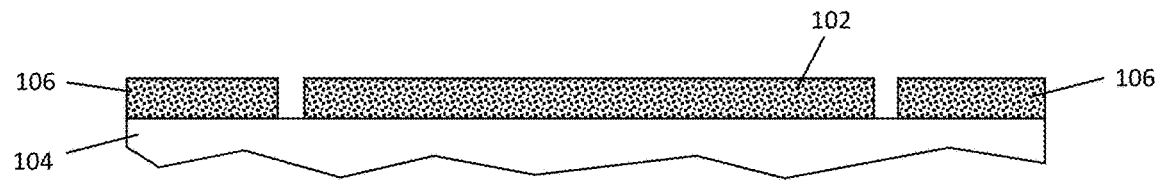
Figures 2, 11:
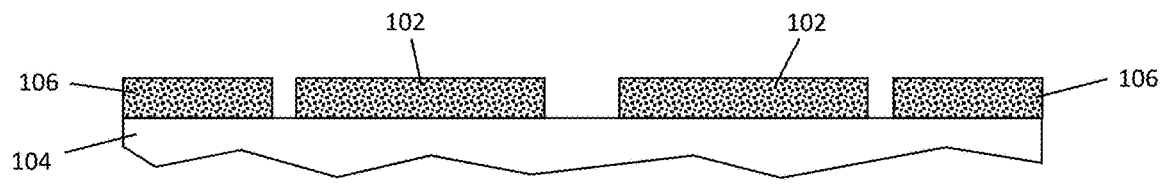
Figures 3, 11:
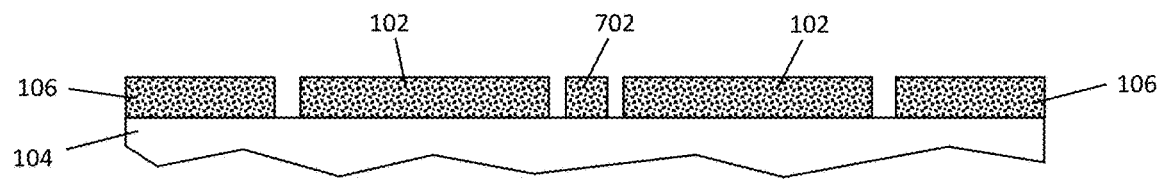
Figures 1, 12:
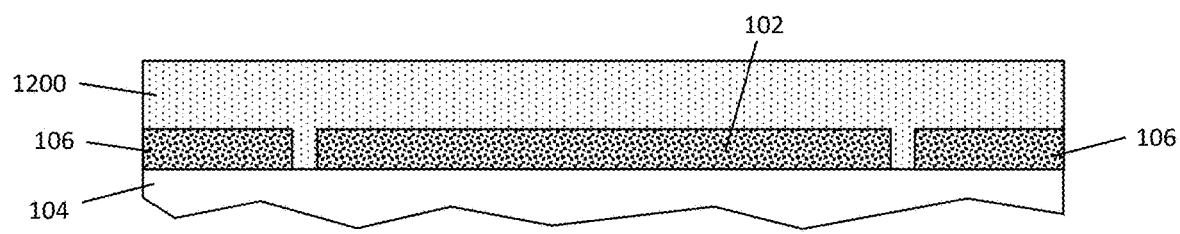
Figures 2, 12:
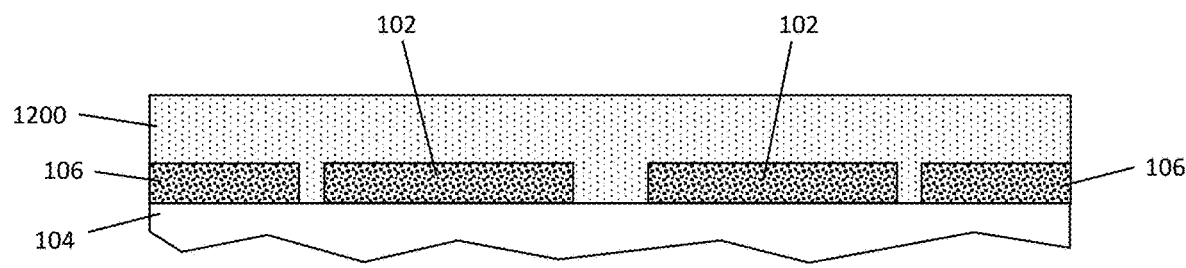
Figures 3, 12:
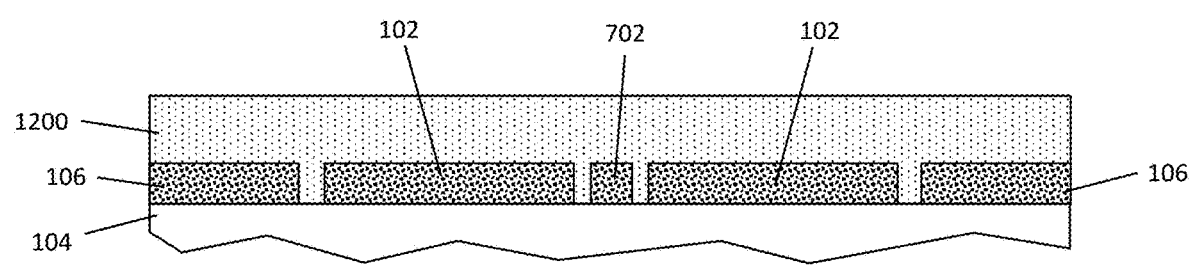

Depending on the specific lower electrode pattern desired, the process may proceed to any of FIG. 11-1, 11-2 or 11-3. For example, in FIG. 11-1, a photolithographic process is used to pattern and etch openings into the electrode layer 1000 so as to define the electrode pattern of FIG. 1, namely a lower electrode 102 and adjacent metal regions 106. In this particular embodiment, a center region of the lower electrode 102 remains intact. FIG. 11-2 illustrates the patterning of the electrode layer 1000 of the FIG. 4 embodiment (i.e., center portion of electrode removed to define a "donut" pattern), and FIG. 11-3 illustrates the patterning of the electrode layer 1000 of the FIG. 7 embodiment (i.e., formation of the additional electrode 702 at the center portion of the donut pattern).

Once the electrode pattern is defined, the process may then proceed to an insulation fill operation as illustrated in FIGS. 12-1, 12-2 and 12-3. As shown, an insulation layer 1200 (e.g., silicon oxide) is formed over the patterned electrode material. The insulation layer 1200 is then planarized as respectively shown in FIGS. 13-1, 13-2 and 13-3 to form the insulator material 108 described above. From this point, processing for each of the illustrated electrode design embodiments is substantially the same. Accordingly, the remaining figures are illustrated in the context of the first embodiment only (i.e., from FIG. 13-1) for conciseness, although it should be understood that the subsequent processes are equally applicable to the other embodiments.

Figures 1, 13:
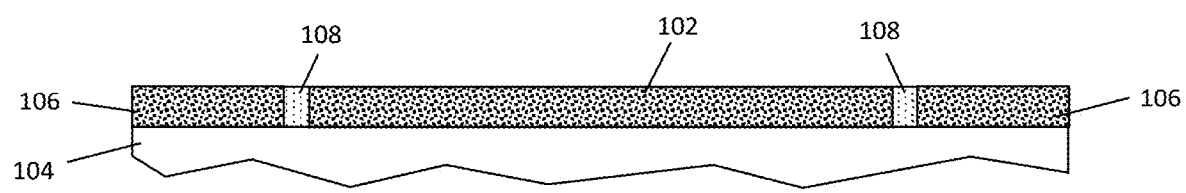
Figures 2, 13:
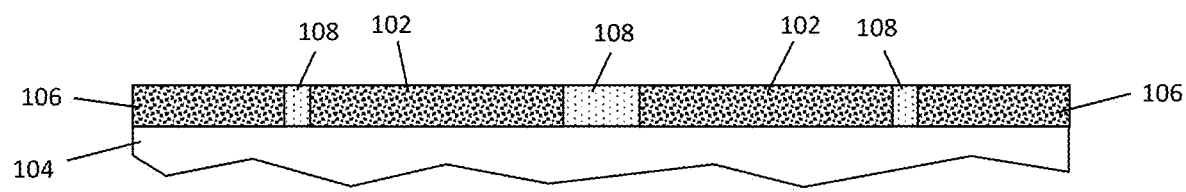
Figures 3, 13:
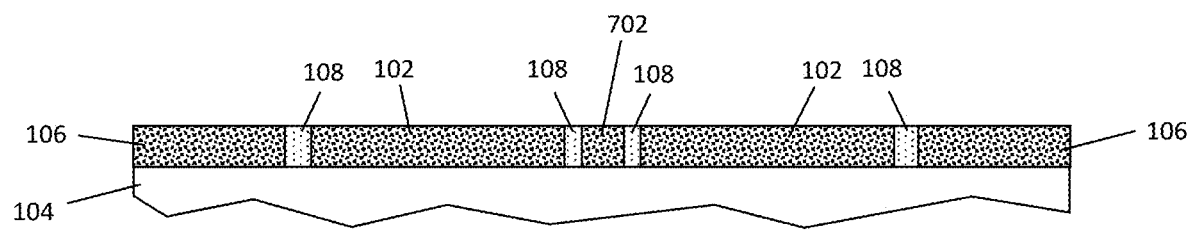
Figure 14:
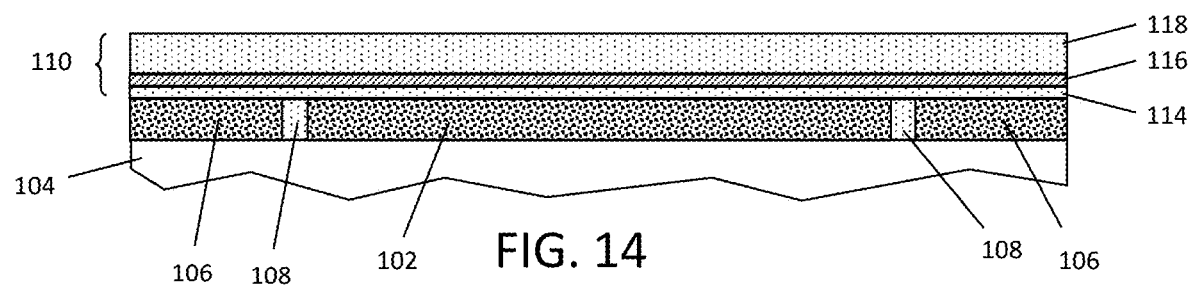

Referring now to FIG. 14, an insulator stack 110 as described above is formed over the lower electrode layer, such as the lower electrode 102 and adjacent metal regions 106 illustrated in FIG. 13-1. In the illustrated embodiment, the insulator stack 110 includes a first oxide layer 114 (e.g., CVD silicon oxide having a thickness of about 1-100 nm) formed over the lower electrode 102 and adjacent metal regions 106, a second oxide layer 116 (e.g., ALD aluminum oxide having a thickness of about 5-100 nm) formed over the first oxide layer 114, and a third oxide layer 118 (e.g., sputter deposited silicon oxide having a thickness of about 1-300 nm) formed over the second oxide layer 116.

Figure 15:
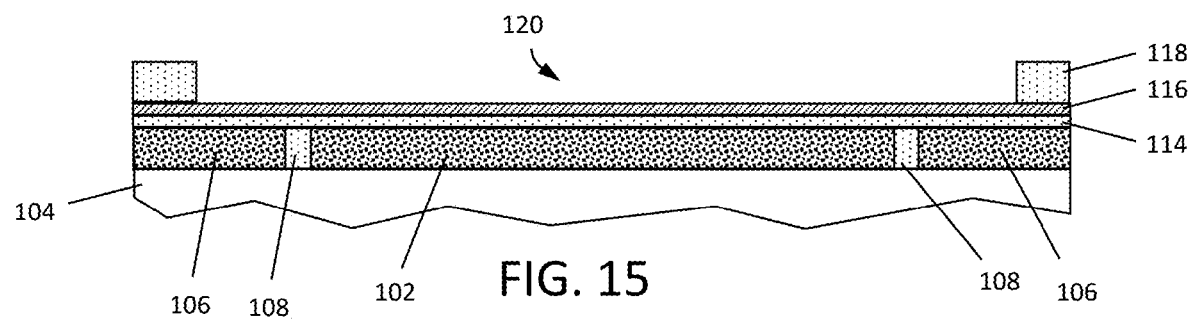

In FIG. 15, a first lithographic patterning and etch process is performed to define the cavity 120 by removing a portion of the third oxide layer 118, using the second oxide layer 116 as an etch stop. As an added benefit, aluminum oxide material of the second oxide layer 116 present at the bottom of the cavity 1500 may also help to reduce charging of a (subsequently formed) top membrane in the event the top membrane comes into contact with the second oxide layer 116 during device operation (e.g., such as during a collapse mode of transducer operation). Optionally, a thin layer of aluminum oxide (not shown) and also a thin self-assembled monolayer (SAM) with a heptadecafluoro tetrahydrodecyl trichlorosilane or dodecyltrichlorosilane precursor (not shown) may be formed on the second oxide layer 116 after patterning and before photoresist removal. A SAM formed at the bottom of the cavity 120 may help to reduce any stiction of the top membrane to the bottom of the cavity 120 in the aforementioned collapse mode of operation or other mode where the top membrane comes in physical contact with the bottom of the cavity 120. It should further be appreciated at this point that although the illustrated embodiments depict a single cavity, any suitable number of cavities and corresponding electrode structures may be formed (e.g., hundreds, thousands, tens of thousands, etc.)

Figure 16:
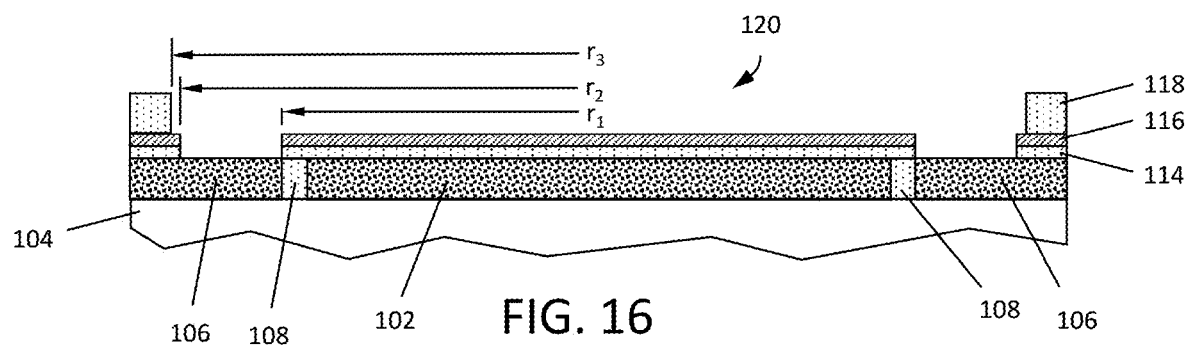

Referring now to FIG. 16, a second lithographic patterning and etch process is performed to expose the adjacent metal regions 106 at the outer perimeter of the cavity 120. The second etch removes a portion of the second oxide layer 116 and first oxide layer 114, stopping on the adjacent metal regions 106, which will serve as a getter material. At this point, the device as depicted in FIG. 16 is prepared for membrane bonding. A particular size or size range of the opening(s) formed through the second oxide layer 116 and first oxide layer 114 (and thus the resulting amount of adjacent metal region material to be exposed) may be chosen based on one or more calculations on how much gas needs to be consumed/gettered during the bonding process. In addition, a determination of how much getter material area to be formed in each cavity may depend on factors such as for example, how much gas is released during the bonding process, the device lifetime, and the desirable cavity pressure after the getter is activated. Final pressure may be adjusted by getter activation, which in turn may be accomplished by annealing at elevated temperatures. In embodiments, it is generally preferable to have more exposed getter material than a targeted amount, rather than less exposed getter material than the target amount, since the annealing time could be shortened with the extra getter material. By way of example only, for a transducer cavity having a cross sectional area of about 0.030 cm$^2$, an example range of getter material area within this cavity for effective gettering maybe about $1 \times 10^{-4}$ cm$^2$ to about $2.5 \times 10^{-4}$ cm$^2$. In embodiments, it may be desirable to build in a further margin for getter material exposure to allow for process variations and calculated getter efficiency. Thus, for this specific example shown in FIG. 16, an inner radius $r_1$ of the getter material (metal regions 106) is about 83 microns (μm), an outer radius $r_2$ of the getter material is about 96 microns μm, and a transducer cavity radius $r_3$ is about 98 μm. With a circular cavity configuration, the resulting getter area is about $7.3 \times 10^{-3}$ cm$^2$, which is roughly an order of magnitude more than an exemplary calculated range needed for a desired gettering capability. Again, it should be appreciated that these values are exemplary only and the disclosure is not limited to such values and ranges.

Figure 17:
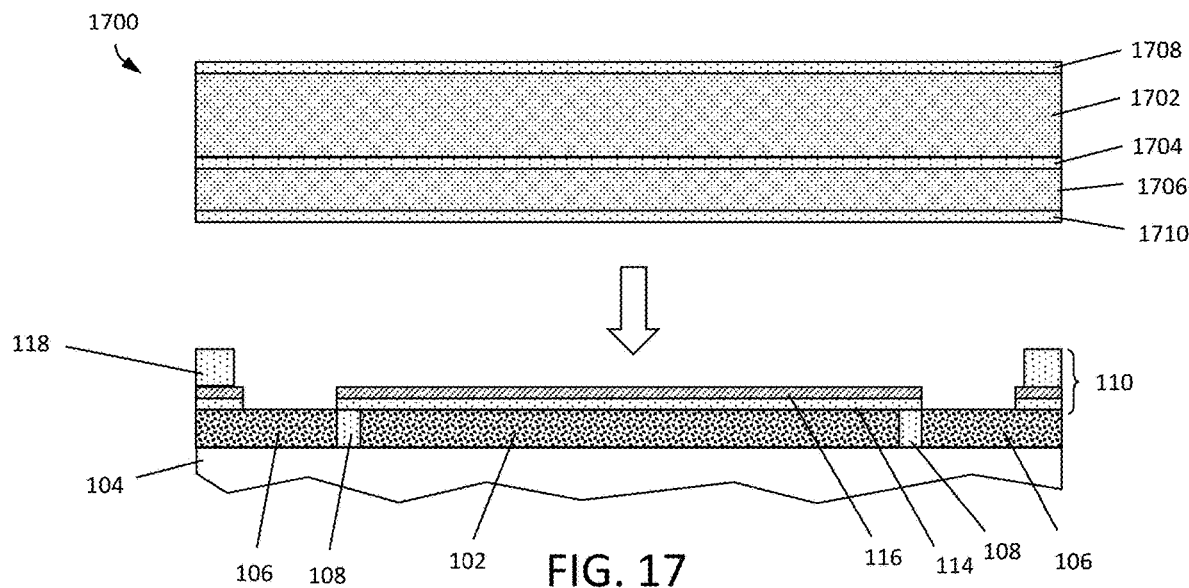

As shown in FIG. 17, a substrate 1700 (e.g., a silicon-on-insulator (SOI) substrate) includes a handle layer 1702 (e.g., a silicon layer), a buried oxide (BOX) layer 1704, and a silicon device layer 1706. An oxide layer 1708 may optionally be provided on a backside of the handle layer 1702. The silicon device layer 1706 may be formed from single crystal silicon and may be doped in some embodiments. Such doping may be highly doped P-type or, alternatively N-type, and may be uniform through the silicon device layer 1706 or patterned by implantation in certain regions. In addition, an oxide layer 1710 (e.g., a thermal silicon oxide) is formed on the silicon device layer 1706.

Figure 18:
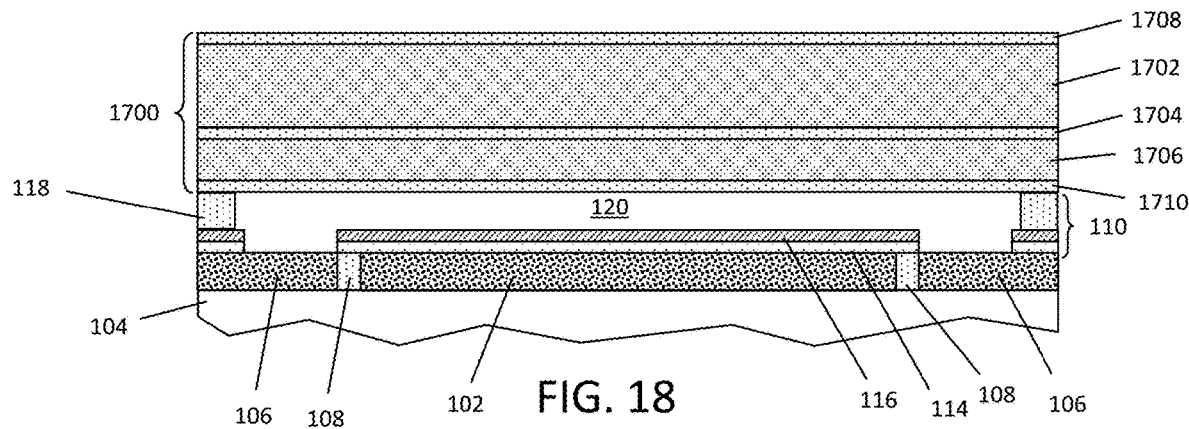
Figure 19:
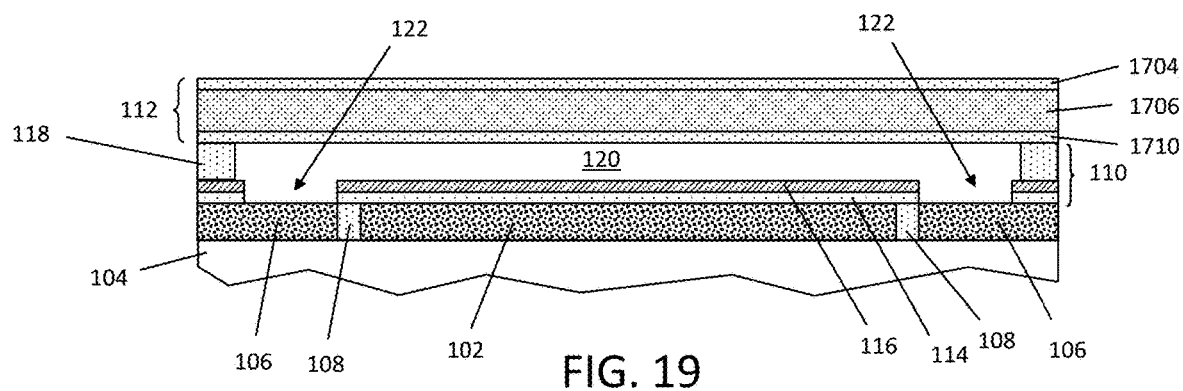

As shown in FIG. 18, the substrate 1700 is bonded to the substrate 104 and the aforementioned structures formed on the substrate 104. In the embodiment depicted, the oxide material of layer 1710 is bonded to the oxide material 118 by low temperature oxide bonding methods (e.g., below 450° C.), which may prevent damage to circuitry of the substrate 104. As stated above, there may be a difference in cavity pressures across the die and wafer due to H$_2$O based byproducts and the propagation of the bond. Because the metal surface of the adjacent metal regions 106 is exposed during bonding of the substrate 1700, the metal is able to consume gases such as oxygen, nitrogen, argon, water vapor, etc., resulting in a more uniform pressure across the various cavities 120 of the ultrasound device.

After bonding, the oxide layer 1708 and the handle layer 1702 are removed by a suitable technique (e.g., etching, grinding, etc.), thereby defining the membrane 112 discussed above and as illustrated in FIG. 19. Optionally, the BOX layer 1704 may also be removed prior to additional processing, which may include suitable steps to complete final wiring, interconnect and/or packaging steps used to produce an ultrasound device.

Figure 20:
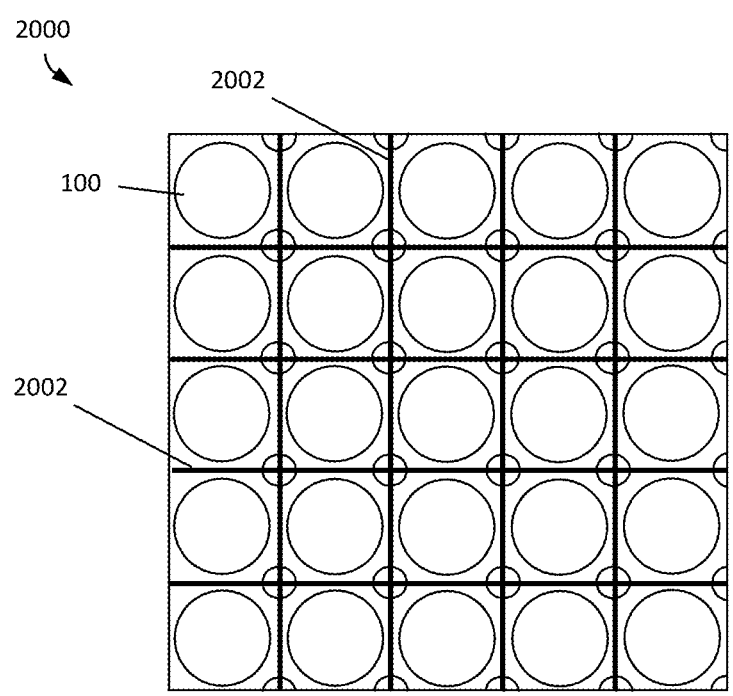
FIG. 20 illustrates a top view of an example ultrasound transducer device formed using any of the process flow sequences described herein.

FIG. 20 illustrates a top view of an example ultrasound transducer device 2000 formed using any of the process flow sequences described herein. As illustrated, the transducer device includes an array of individual transducers 100, such as those described above. The specific number of transducers 100 shown in FIG. 20 should not be construed in any limiting sense, and may include any number suitable for a desired imaging application, which may be for example on the order of tens, hundreds, thousands, tens of thousands or more. It will be appreciated the above described gettering techniques are particularly beneficial with an increasing larger array, given the ability to provide a uniform cavity pressure across a wafer or die. FIG. 20 further illustrates an example location of metal 2002 that may distribute an electrical signal to the membranes (upper electrodes) of the transducers 100.

It should be appreciated that although the exemplary embodiments illustrate and describe a same bottom electrode metal material used as a getter material during membrane bonding, other non-metallic or non-metallic alloy getter materials may also be used in a similar manner. For example, graphite, phosphorous and/or certain salts may serve as a cavity getter material. Moreover, with respect to the specific placement of a getter material, other locations in addition to a cavity bottom are also contemplated. For example, with additional processing operations, layers may be formed in a manner so as to have getter material disposed on cavity sidewalls and/or the membrane itself (top of sealed cavity) for gettering during membrane bonding. Such additional getter layer(s) may also be formed at a different level than the bottom electrode material.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, features described in one embodiment may be combined in any manner with features described in other embodiments.

Also, certain aspects may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. A method of forming an ultrasound transducer device, the method comprising:
   forming one or more insulating layers over a bottom electrode and over a getter material;
   removing the one or more insulating layers from the getter material;

bonding a membrane to a substrate so as to form a sealed cavity therebetween, wherein a surface located within and exposed to the sealed cavity comprises the getter material.

2. The method of claim 1, wherein the surface exposed to the sealed cavity comprises a top surface of the substrate.

3. The method of claim 1, wherein the getter material comprises a same material as the bottom electrode.

4. The method of claim 1, wherein the getter material comprises one or more of: titanium, zirconium, vanadium, cobalt, nickel, and alloys thereof.

5. The method of claim 1, wherein the getter material is electrically isolated from the bottom electrode.

6. The method of claim 4, wherein the getter material is disposed at an outer perimeter of the cavity.

7. The method of claim 4, wherein the cavity is circular shaped and the getter material is disposed at an outer radius of the cavity.

8. The method of claim 1, wherein the getter material is configured to remove one or more of oxygen, nitrogen, argon, or water vapor from the cavity.

9. An ultrasound transducer device, comprising:
a membrane bonded to a substrate with a sealed cavity therebetween wherein a surface located within and exposed to the sealed cavity comprises a getter material;
one or more insulating layers formed over a bottom electrode of the cavity but not present over the getter material.

10. The device of claim 9, wherein the surface exposed to the sealed cavity comprises a top surface of the substrate.

11. The device of claim 9, wherein the getter material comprises one or more of: titanium, zirconium, vanadium, cobalt, nickel, and alloys thereof.

12. The device of claim 9, wherein the getter material is electrically isolated from the bottom electrode of the cavity.

13. The device of claim 11, wherein the getter material is disposed at an outer perimeter of the cavity.

14. The device of claim 11, wherein the cavity is circular shaped and the getter material is disposed at an outer radius of the cavity.

15. The device of claim 9, wherein the getter material is selected to remove one or more gases including one or more of oxygen, nitrogen, argon, or water vapor.

16. The device of claim 9, wherein the getter material comprises a same material as the bottom electrode of the cavity.

* * * * *